United States Patent
Tetsuka

(10) Patent No.: US 9,402,578 B2
(45) Date of Patent: Aug. 2, 2016

(54) CRANK ANGLE INDICATING SYSTEM

(71) Applicant: Shimano Inc., Sakai-shi, Osaka (JP)

(72) Inventor: Toshio Tetsuka, Hyogo (JP)

(73) Assignee: Shimano Inc., Sakai-shi (JP)

( * ) Notice: Subject to any disclaimer, the term of this patent is extended or adjusted under 35 U.S.C. 154(b) by 0 days.

(21) Appl. No.: 14/498,743

(22) Filed: Sep. 26, 2014

(65) Prior Publication Data

US 2016/0089072 A1 Mar. 31, 2016

(51) Int. Cl.
- *G09B 9/00* (2006.01)
- *A61B 5/22* (2006.01)
- *A63B 22/06* (2006.01)
- *G01L 3/10* (2006.01)

(52) U.S. Cl.
CPC ............. *A61B 5/221* (2013.01); *A63B 22/0605* (2013.01); *G01L 3/10* (2013.01); *A63B 2220/16* (2013.01)

(58) Field of Classification Search
CPC ........................................................ A61B 5/221
USPC ..................... 340/427, 432; 482/57
See application file for complete search history.

(56) References Cited

U.S. PATENT DOCUMENTS

| | | | |
|---|---|---|---|
| 4,856,996 A * | 8/1989 | Henson | A63B 24/00 434/61 |
| 2010/0024590 A1 | 2/2010 | O'Neill et al. | |
| 2012/0330572 A1 | 12/2012 | Longman | |
| 2013/0019700 A1 | 1/2013 | Matsumoto | |
| 2013/0030629 A1* | 1/2013 | Suzuki | B62M 6/50 701/22 |
| 2014/0283622 A1* | 9/2014 | Namiki | B62M 3/00 73/862.53 |
| 2014/0315693 A1* | 10/2014 | Randle | A63B 22/0605 482/57 |
| 2015/0025816 A1* | 1/2015 | Ross | A61B 5/1038 702/44 |

* cited by examiner

*Primary Examiner* — Brent Swarthout
(74) *Attorney, Agent, or Firm* — Alleman Hall McCoy Russell & Tuttle LLP

(57) ABSTRACT

A crank angle indicating system is provided for a pedaling device. The crank angle indicating system may include a crank angle detector configured to detect a crank angle of a crankshaft of a pedaling device, and an indication device configured to output at least one of an aural and a haptic indicator when a predetermined crank angle is reached, allowing a cyclist to time the application or release of force to the pedals accordingly.

19 Claims, 9 Drawing Sheets

CRANK ANGLE INDICATING SYSTEM

BACKGROUND

For cyclists, correct pedaling technique is a central component of a good training regimen. By increasing the force applied to the pedals at certain positions of the pedal crank cycle, the cyclist may achieve optimum efficiency and power output during pedaling. However, achieving an optimum timing of the application of pedal force can be an elusive goal.

In one prior system to aid cyclists in this regard, a crank angle is measured via a crank angle sensor, and then a visual indicator is displayed on a display of a bicycle computer mounted to the handlebar of the bicycle, when the crank is at a certain angle. This approach suffers from the drawback that it requires the cyclist to concentrate attention on a display that is provided on a handlebar or wrist, which may be inconvenient when the cyclist desires to focus attention elsewhere during a training session.

SUMMARY

To address the above issues, a crank angle indicating system is provided. According to a first aspect of the invention, the crank angle indicating system may comprise a crank angle detector configured to detect a crank angle of a crankshaft of a pedaling device, and an indication device that is configured to output at least one of an aural and a haptic indicator upon the detected crank angle reaching a predetermined crank angle. One potential advantage of this configuration is that the cyclist receives a cue to apply and/or release force on the pedal at the appropriate moment in the spin cycle of the crank gear.

In the first aspect, the predetermined crank angle may be set according to a user configurable setting. One potential advantage of this configuration is that the cyclist can time the application and release of force on the pedals at different positions of the crank gear and optimize the settings to adapt to different technique workouts.

In the first aspect, the predetermined crank angle may be a first predetermined crank angle and the crank angle detector may further be configured to detect a second predetermined crank angle. The indication device is configured to output at least one of an aural and a haptic indicator upon the detected crank angle reaching the first predetermined crank angle and the second predetermined crank angle, respectively. One potential advantage is that the system can indicate angles at which force should be applied to each of the right and left pedals using these first and second predetermined angles, for example.

In the first aspect, the second predetermined crank angle may be set according to a user configurable setting. One potential advantage of this configuration is that the cyclist can time the application and release of force on the pedals at different positions of the crank gear and optimize the settings to adapt to different technique workouts.

In the first aspect, the first predetermined crank angle and the second predetermined crank angle may be different angles. One potential advantage is that the system can indicate different positions within the rotation of the pedals at which force should be applied, either during a pedal downstroke or upstroke, for example.

In the first aspect, the left and right predetermined crank angles may be substantially separated by 180 degrees. The 180 degree separation enables the system to indicate an angle at which force should be applied in the downstroke for both the right and left pedals.

In the first aspect, the first indicator and the second indicator may be aurally or haptically distinguishable. One potential advantage of this configuration is that the cyclist can distinguish between the first and second indicators, enabling the cyclist to quickly understand their meaning. For example, one indicator may be meant for the left foot and the other for the right foot, or one may be meant for the downstroke and the other for the upstroke, etc.

In the first aspect, at least one of an aural and a haptic indicator may be emitted over a rotational angle range of the detected crank angle. One potential advantage of this configuration is that it can indicate to the cyclist not only an initial timing, but also a range over which force should be applied. In addition, such an indicator may be more conspicuous to the cyclist and thus more difficult to miss.

In the first aspect, an aural or haptic characteristic of at least one of an aural and a haptic indicator may vary while being emitted over the rotational angle range. One potential advantage of this configuration is that the varying characteristic of the indicator can indicate to the rider a desired peaking or waning intensity for the application of force, for example. In addition, the varying characteristic may be more conspicuous to the cyclist and thus more difficult to miss.

In the first aspect, the crank angle indication system may comprise a processor executing program logic, configured to receive the detector signal from the crank angle detector indicating a detected crank angle, and output an angle indication signal upon determining that the detected crank angle reaches a predetermined crank angle. Furthermore, the indication device may be configured to receive the angle indication signal and, in response, output at least one of an aural and a haptic indicator. One potential advantage of this configuration is that the processor provides a reliable configuration to seamlessly convey information from the crank angle detector to the indication device.

In the first aspect, the processor may be a processor of an onboard computing device mountable to the pedaling device. One potential advantage of this configuration is that the processor may be installed on the pedaling device, rather than carried in the clothing of the cyclist or mounted externally to the pedaling device, for example. This is particularly useful when the pedaling device is a mobile bicycle rather than a stationary trainer.

In the first aspect, an input device may be configured to selectively activate and deactivate the indication device. One potential advantage of this configuration is to provide an easy method to turn off any aural or haptic indication device when the pedaling device is not being used for training.

In the first aspect, at least one of the aural and haptic indicator may be an aural indicator, and the indication device may be a speaker that emits the aural indicator. One potential advantage of this configuration is that the cyclist will not need to concentrate attention on a visual display when the cyclist is focusing attention elsewhere during a training session.

In the first aspect, the speaker may be located on an onboard computing device coupled to the pedaling device. The configuration combining the speaker with the onboard computing device achieves the potential advantage of reducing the number of components that require attachment to the pedaling device.

In the first aspect, the speaker may be located in an earphone. This adds the potential advantage of providing the cyclist with a personalized signal that is not generally audible to other cyclists or bystanders.

In the first aspect, at least one of the aural and haptic indicator may be a haptic indicator, and the indication device may be a vibration device configured to emit vibration as the haptic indicator. Vibration has the potential advantage that it is a personalized form of signaling not perceptible by bystanders. Further, vibration does not require a speaker or earphone for transmission, thus enabling the cyclist to hear other sounds in the environment, such as instructions from coaching staff or the cheers of spectators, without interruption.

In the first aspect, the vibration device may be coupled for vibrational transmission to at least one of a handlebar of the pedaling device, a seat of the pedaling device, a pedal of the pedaling device, and wristwatch of a rider of the pedaling device. One potential advantage of this configuration is that the haptic indicator from the vibration device can be easily felt by the cyclist since the cyclist's hands, posterior, feet and wrist are in contact with these components and devices.

In the first aspect, a crank angle detector may be configured to detect a crank angle of a crankshaft of a pedaling device, and an indication device is configured to output an indicator to provide a cue for a cyclist to apply or release force on the pedals based on the current crank angle of the crankshaft of the pedaling device. One potential advantage of this configuration is that the cyclist can practice optimizing the pedaling stroke to achieve optimum efficiency and power output during pedaling.

According to a second aspect, a crank angle indicating system may be provided, which includes a crank angle detector configured to detect a crank angle of a crankshaft of a pedaling device, and an indication device configured to output an indicator to provide a cue for a rider to apply and/or release force on the pedals based on a current crank angle of the crankshaft of the pedaling device. One potential advantage of this configuration is that the cyclist receives a cue to apply and/or release force on the pedal at the appropriate moment in the spin cycle of the crank gear.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

BRIEF DESCRIPTION OF THE DRAWINGS

The present disclosure is illustrated by way of example and not by way of limitation in the figures of the accompanying drawings, in which the like reference numerals indicate like elements and in which:

FIG. 1 is drawn approximately to scale unless otherwise indicated; however, other relative dimensions may be used, if desired.

DETAILED DESCRIPTION

A selected embodiment of the present invention will now be described with reference to the accompanying drawings. It will be apparent to those skilled in the art from this disclosure that the following description of an embodiment of the invention is provided for illustration only and not for the purpose of limiting the invention as defined by the appended claims and their equivalents.

Figure 1:
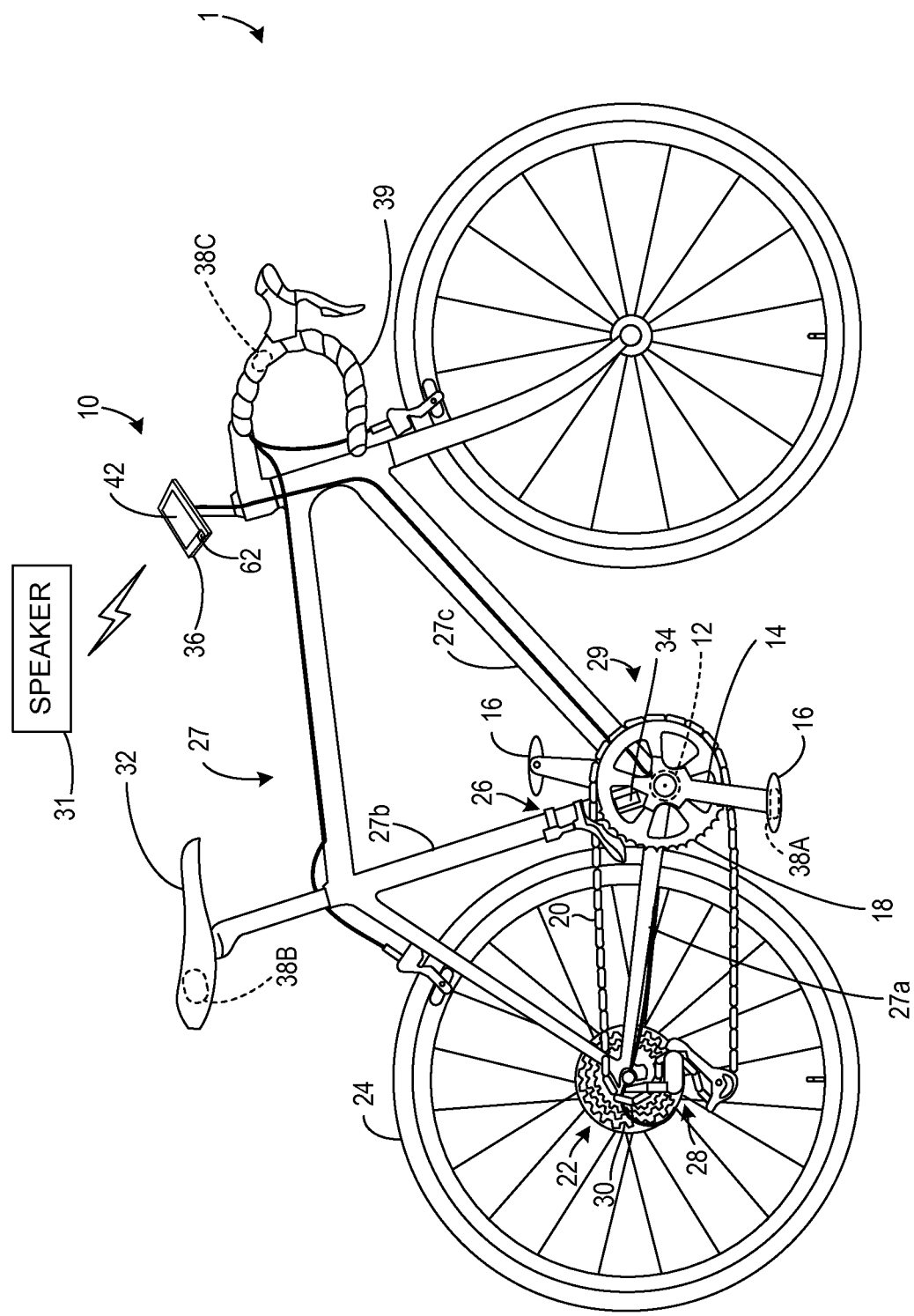
FIG. 1 shows a side view of an example pedaling device.

Referring initially to FIG. 1, a pedaling device 1 is illustrated that uses includes a crank angle indicating system 10 according to one example embodiment. The pedaling device 1 is illustrated as a bicycle, but may encompass other pedaling devices 1 such as stationary bicycle trainers, etc., as discussed below. The pedaling device 1 includes, among other things, a crankshaft 12 coupled by crank arms 14 to pedals 16. The crankshaft 12 is coupled to co-rotate around a crankshaft axis (not shown) with one or more chain rings 18, and drive a chain 20, when force is applied to pedals 16. Power is transmitted via the chain 20 to a rear sprocket assembly 22, which drives rotation of the rear wheel 24. A front derailleur 26 may be provided to transition among a plurality of chain rings 18 that co-rotate with the crank arms 14, and a rear derailleur 28 may be provided to transition among a plurality of sprockets 30 of the rear sprocket assembly 22, to thereby impart a gearing ratio to the pedaling device 1. The pedals 16, crank arms 14, chain rings 18, chain 20, and rear sprocket assembly 22, form a drive train 29 configured to convert the cyclist's pedaling force into a driving force applied to the rear wheel to propel the bicycle forward. While a multi-geared pedaling device is shown, it shall be understood that only a single front chain ring and rear sprocket may be provided, such that the pedaling device operates with a single gear ratio. The various components of the drive train 29 are mounted to a frame 27 of the bicycle.

The crank angle indicating system 10 includes a crank angle detector 34 that is provided on the pedaling device 1 and configured to detect a crank angle of the crankshaft 12. The crank angle detector 34 may utilize a sensor such as a magnetic sensor, optical sensor, or accelerometer to detect the rotation of crankshaft 12 and the crank angle. The crank angle detector 34 may be mounted in various locations that are proximate the crankshaft 12 or a component that co-rotates with the crankshaft 12, such as the crank arm 14, pedals 16, or chain ring 18. For example, the crank angle detector 34 may be mounted within or on a bottom bracket (not shown), or on a chain stay 27a, seat tube 27b, or down tube 27c, of the frame 27.

The crank angle indicating system 10 further includes a computing device 36, which may be in the form of a bicycle computer, as discussed below. In one embodiment, the crank angle detector 34 is coupled by a conductor to and communicates with an input/output module of the computing device 36. In other embodiments, the coupling between the computing device 36 and crank angle detector 34 may be wireless. The computing device 36 is mountable to the handlebar 39 or other suitable location on the pedaling device 1.

The computing device 36 typically includes an associated display 42. The display 42 and computing device 36 are provided at a suitable location such as on the handlebar 39 so that the user may reach the computing device 36 and input predetermined crank angles according to a user configurable setting. Typically, the computing device 36 and the associated display 42 are compartmentalized in the same unit housing; however, in other embodiments, the display 42 may be provided separately from the computing device. For example, the computing device 36 may be configured to communicate with a cyclist's smartphone, which may act as the display 42. Further, computing device 36 may include an associated an input device (not shown). The input device may be physical buttons or keys of the computing device, or virtual buttons displayed on display device 42, which may be touch sensitive.

The crank angle indicating system 10 further includes an indication device 38. The computing device 36 communicates with the indication device 38, and the indication device 38 is configured to emit an indicator that a particular crank angle or range of crank angles has been met, as described below. The indication device 38 may be provided at a suitable location on the pedaling device 1, such as on a seat 32, handlebar 39, frame 27 or the pedals 16. While typically formed separate from the computing device 36, it will be appreciated that the indication device 38 may be formed integrally with the computing device 36 in an alternative embodiment. An input control, such as a physical button or hard switch 62, or a virtual button or switch (not shown) displayed on a touch sensitive display of the computing device 36, etc., may be provided so as to be integrated with the indication device 38 or formed separately therefrom, and may be configured to selectively activate and deactivate the indication device 38 in response to input from a cyclist.

The indication device 38 may be an aural output device 56 (see FIG. 2), such as a speaker 31 that emits an aural indicator, which is configured to output an aural indicator when the predetermined crank angle is reached. In certain embodiments, the speaker 31 may be located on a computing device 36 that is onboard and coupled to the pedaling device 1. In other embodiments, the speaker 31 may be located in an earphone. The earphone may be integrated within a helmet of the cyclist, and may receive signals via a wired or wireless connection directly with the computing device 36, or via a wired or wireless connection indirectly via another intermediate device with which the computing device 36 communicates, such as a cyclist's smartphone, for example.

Alternatively, the indication device 38 may be a haptic output device 56 (see FIG. 2), in which a haptic indicator is outputted when the predetermined crank angle is reached. The haptic output device is typically a vibration device that is coupled for vibrational transmission to at least one of a handlebar 39 of the pedaling device 1 (see handlebar-coupled haptic output device 38C), a seat 32 of the pedaling device (see seat-coupled haptic output device 38B), one or both pedals 16 of the pedaling device (see pedal-coupled haptic output device 38A), and a wristwatch (not shown) of a rider on the pedaling device 1, the wristwatch being in direct or indirect (e.g., via a smartphone) wireless communication with the computing device 36. Alternatively, the haptic output device may be coupled to the pedaling device 1 at another suitable location for vibrational transmission to the cyclist.

Figure 2:
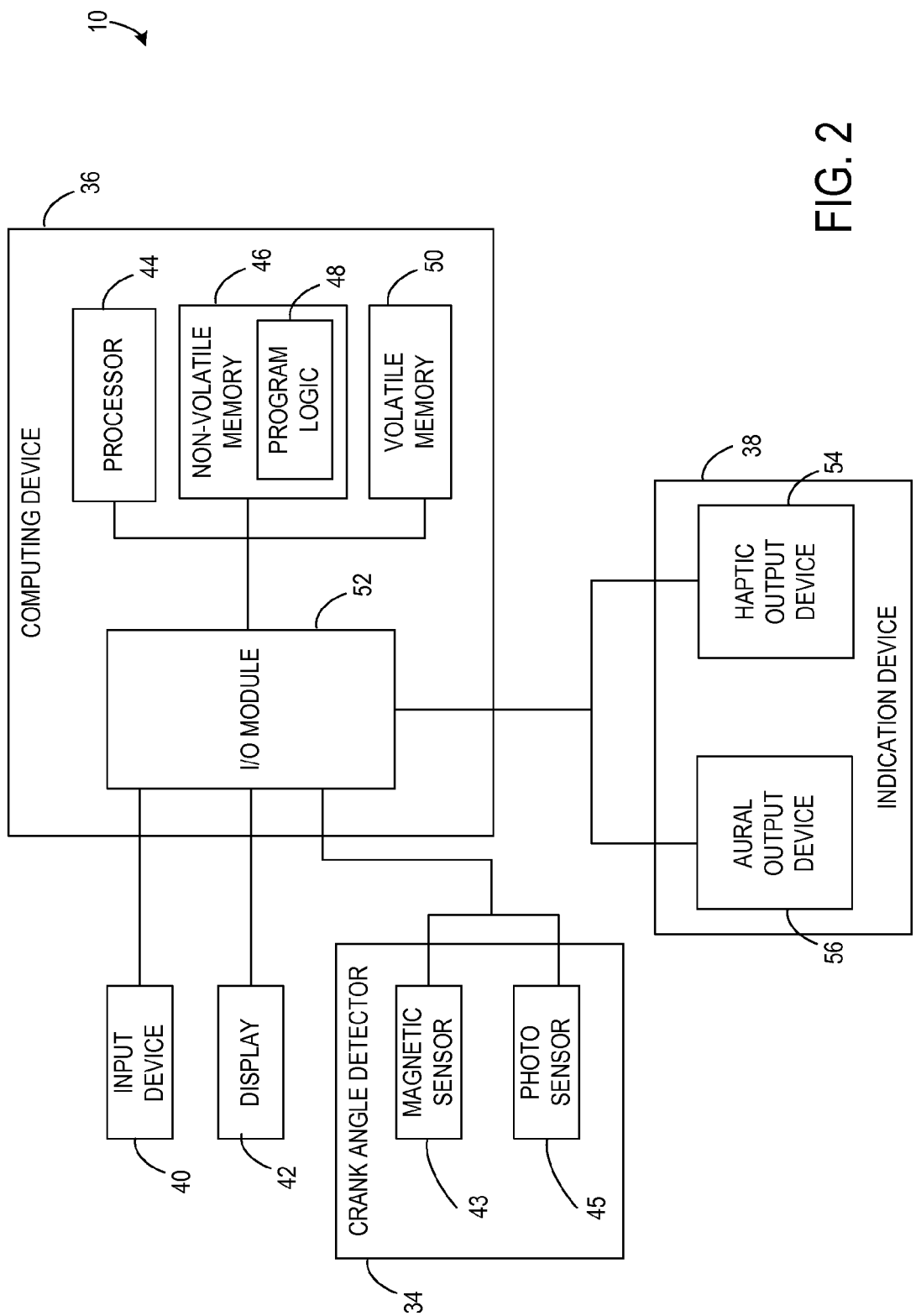
FIG. 2 is a block diagram relating to the crank angle detector, the computing device, and the indication device, in accordance with an embodiment of the present disclosure.

Referring to FIG. 2, an exemplary onboard computing device 36, mountable to the pedaling device 1, is provided with an input/output module 52 which communicates with a processor 44, a non-volatile memory 46 containing stored program logic 48, and volatile memory 50. The input/output module 52 receives as input, a detector signal from the crank angle detector 34 and sends an angle indication signal to the indication device 38 when the crankshaft has reached a predetermined crank angle, under the command of program logic 48 executed by processor 44 using portions of the volatile memory 50.

The crank angle detector 34 may include a magnetic sensor 43 or an optical sensor 45, which is coupled by a conductor to an input/output module 52, or alternatively is wirelessly coupled to the input/output module 52. The indication device 38, which is configured to output at least one of an aural and a haptic indicator through an aural output device 56 or a haptic output device 54, respectively, upon the detected crank angle reaching a first predetermined crank angle, in one mode of operation sustains the indicator until the second predetermined crank angle is reached and the second angle indication signal is received, as discussed below. The indication device 38 may be directly coupled to the computing device 36 or coupled via an intermediate device such as a smartphone, as discussed above. Input device 40 receives user input for example via a touch sensitive display 42 or a physical button, for example, and sends the user input to the computing device 36 via the input/output module 52. Display device 42 receives display signals from the computing device 36 via the input/output module 52, which causes graphical output such as a graphical user interface (GUI) to be displayed on the display 42. The input device 40 may accept a wide variety of input and may include predetermined crank angles that are set according to a user configurable setting, as discussed below.

The input device 40 is preferably a touch screen on an interactive display device, but may also be a keyboard, mouse, microphone, etc. The display 42 is preferably a touch sensitive display of computing device 36, but may also be a television, computer screen, wristwatch, mobile phone, etc. The input device 40 and display 42 are preferably compartmentalized into one interactive display device executing a graphical user interface (GUI), but the input device 40 may be provided separately from the display 42 in other embodiments.

The volatile memory 50 may include one or more memory modules and comprise random access memory (RAM), programmable read-write memory, and/or solid state memory. The non-volatile memory 46 may include one or more memory modules and comprise read only memory (ROM), programmable read only memory (PROM), and/or solid state memory. The non-volatile memory may record data for later analysis. Specifically, it could record the values measured from the crank angle detector at various points in time, allowing detailed analysis of pedaling style, including variations in power and cadence between the left and right pedals. This information could help the cyclist identify areas where improvements in performance and pedaling efficiency could be achieved. The processor 44 may be a central processing unit, co-processor units, single core, multi-core, system on chip, application-specific integrated circuit (ASIC), field-programmable gate array (FPGA), or any other suitable logic hardware. The processor 44 is responsible for processing data for the crank angle indicating system 10. This data includes user input from the input device 40 and detector signals from the crank angle detector 34. The processor 44 executes program logic 48 configured to receive the detector signal from the crank angle detector 34, which indicates a detected crank angle, and output an angle indication signal upon determining that the detected crank angle has reached a predetermined crank angle. The processor 44 also calculates power output, torque, cadence, and other metrics of the pedaling device based on the data received from the crank angle detector and sends output to the display 42.

Figure 3:
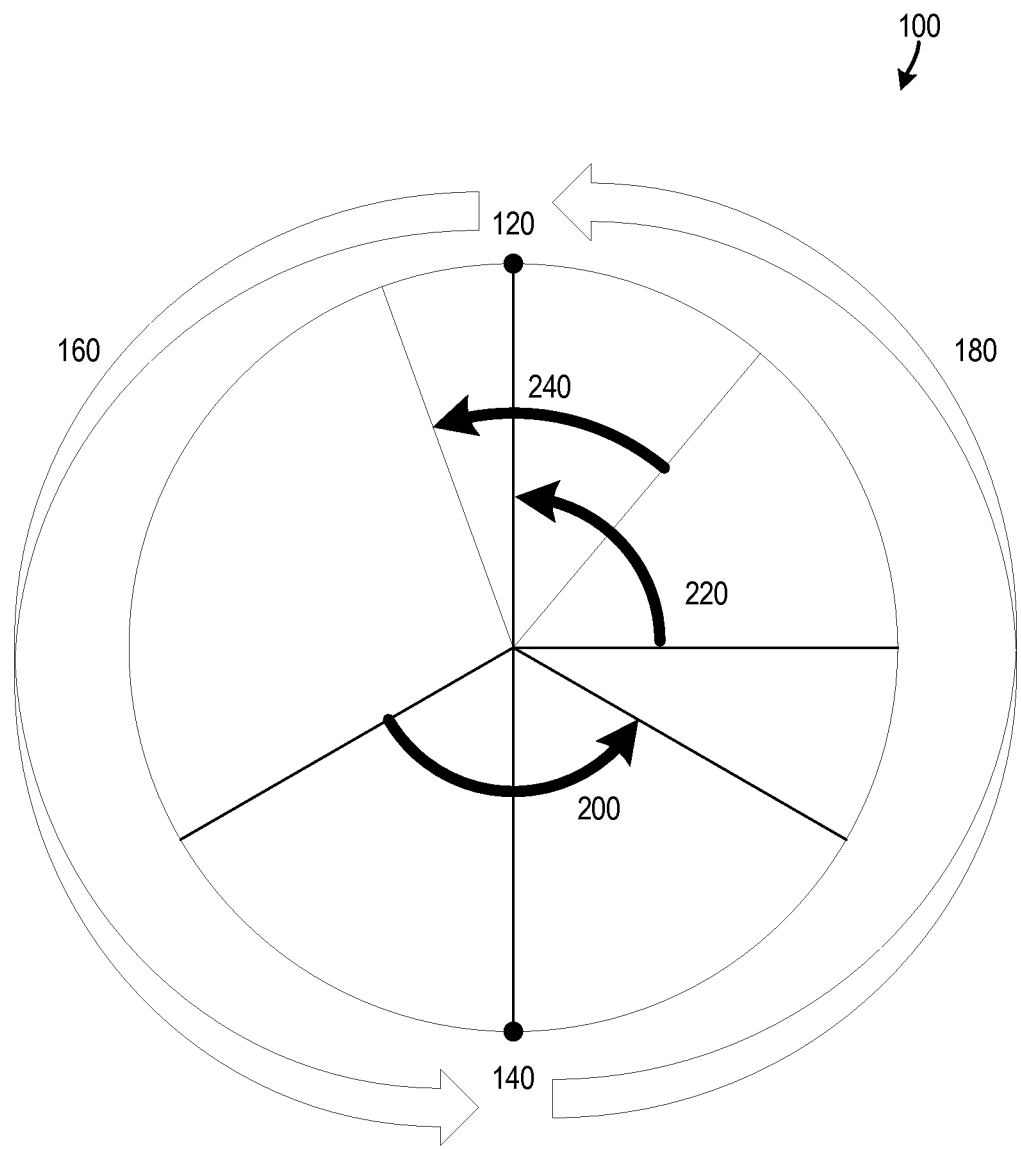
FIG. 3 is a schematic representation of the phases of the pedal crank cycle.

Referring to FIG. 3, a schematic representation of the pedal crank cycle 100 is shown. The downstroke begins at the top dead center 120 as the foot and pedal move towards the bottom dead center 140, often preferably exerting a relatively constant, even force on the pedal throughout the stroke. To maximize power and efficiency, cyclists train to perfect the application of force on the pedal in this phase at an appropriate timing. Thus, the predetermined crank angles when the indication device 38 outputs at least one of an aural indicator and a haptic indicator may be a first predetermined crank angle that is a left predetermined crank angle and a second predetermined crank angle that is a right predetermined crank angle. A first sound, which is an aural indicator emitted when the crank angle becomes a first predetermined crank angle, and a second sound, which is an aural indicator emitted when the crank angle becomes a second predetermined crank angle, may be different from each other. A first haptic feedback, which is a haptic indicator generated when the crank angle becomes a first predetermined crank angle, and a second haptic feedback, which is a haptic indicator generated when the crank angle becomes a second predetermined crank angle, may be different from each other. The first and second predetermined crank angles may be different from each other, and for example may be separated by 180 degrees. For example, the first predetermined crank angle may be set to top dead center 120 and the second predetermined crank angle may be set to bottom dead center 140, which are substantially separated by 180 degrees. Alternatively, the angles may be set when the crank arms are substantially horizontal, or may be separated by a different number of degrees than 180. The first predetermined crank angle and second predetermined crank angle are set via user configurable settings, and thus numerous other crank angle settings are possible.

The indication device 38 is configured to output an indicator and provide a cue for the cyclist to apply or release force on the pedals based on a current crank angle of the crankshaft of the pedaling device, and the device is configured to output at least one of an aural indicator and a haptic indicator upon the detected crank angle reaching the first predetermined crank angle and the second predetermined crank angle, respectively. Thus, an aural indicator or haptic indicator is emitted over the rotational angle range between the predetermined crank angles, ensuring that the cyclist will be notified that the current crank angle at an appropriate timing, such as when the crank angle is within the downstroke phase 160 of the pedal crank cycle 100. This may help the cyclist, for example, apply force in a desired manner at the timing, for improved pedal technique.

The aural characteristic of the aural indicator may vary while being emitted over the rotational angle range; likewise, the haptic characteristic of the haptic indicator may also vary while being emitted over the rotational angle range. In addition, the system may be configured to emit an aural and haptic indicator concurrently in some embodiments for improved notification to the cyclist. Further, the system may be configured to indicate an aural indicator at one predetermined crank angle or crank angle range, and a haptic indicator at another predetermined crank angle or crank angle range.

It will be appreciated that the first and second predetermined crank angles may be set over various other rotational angle ranges according to the cyclist, for example if the cyclist desires to emphasize other phases of the pedal crank cycle 100 in specific technique workouts. For example, the backstroke 200 may range from approximately 120 to 220 degrees and is a transitional phase between the downstroke 160 and the upstroke 180. The upstroke 180 begins at the bottom dead center 140 as the foot and pedal move towards the top dead center 120, and cyclists may train to emphasize pulling upward from 270 to 360 degrees in the recovery phase 220. Lastly, the overstroke 240 is a transitional phase between the upstroke 180 and the downstroke 160, when the cyclist presses forward from approximately 320 to 20 degrees. Thus, by allowing the cyclist to try different settings for the left and right predetermined crank angles, the cyclist can then customize the crank angle indicating system to output an indicator for a specific phase of the pedal crank cycle 100 that is adapted to a specific technique workout. Further, the cyclist may select a third and fourth predetermined crank angle, so that the system is also configured to output at least one of an aural and a haptic indicator upon the detected crank angle reaching the third predetermined crank angle and the fourth predetermined crank angle, respectively. The sounds or haptic feedback corresponding to the third and fourth predetermined crank angles may be different from each other or may be different from the sounds or haptic feedback corresponding to the first and second predetermined crank angles.

Figure 4:
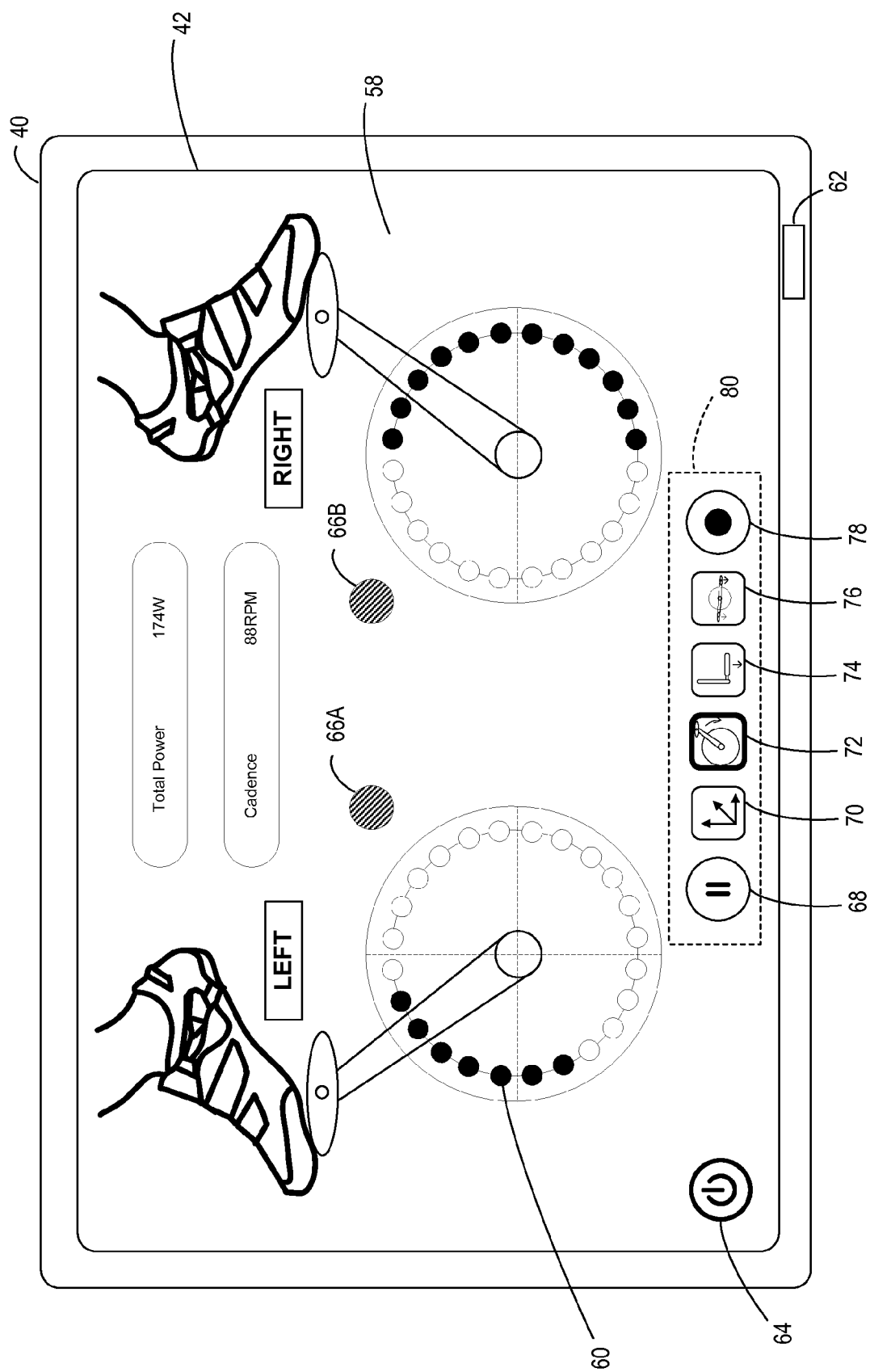
FIG. 4 is a schematic view of a graphical user interface (GUI) preferably executed on an interactive display device, where the user may input predetermined crank angles according to a user configurable setting.

Referring to FIG. 4, computing device 36 may be configured to display a graphical user interface (GUI) 58 to be shown on the display 42 that is mounted on a handlebar of the pedaling device. In the embodiment of FIG. 4, the display 42 is a touch sensitive display with an integrated input device 40 and is capable of both displaying information for the cyclist and receiving touch input from the cyclist, including predetermined crank angles according to the user configurable setting. The cyclist operates the input device 40 by touching areas of the display corresponding to the GUI 58, touch controls, selectors, menus, dialogs, etc. On the GUI 58, a selector 60 divides the pedal crank cycle into a plurality of divisions, each representing a range of degrees of the crank rotation. In the depicted embodiment, there are 24 divisions each representing 15 degrees of crank rotation. The positions of the divisions are determined relative to the positions of the top dead center and the bottom dead center, which may be defined relative to gravity in embodiments that sense crank angle using accelerometers or otherwise have a sensor input to sense gravitational force. Each division is independently configurable by the user to be the left or right predetermined crank angles that determine the rotational angle range that is reached for the indication device to output an indicator. In a 360 degree crankshaft rotation with zero being defined at top dead center for the left crank arm, the left crank arm will reach top dead center at zero degrees and the right crank arm will reach top dead center at 180 degrees, for example. The GUI 58 may provide a hard switch 62 (i.e., a physical button) or a soft button 64 to selectively activate and deactivate the indication device 38. Using this, a cyclist may turn off the indications during a training ride, for example. Other hard or soft buttons may be provided to adjust the crank angles, etc. The GUI 58 may also display metrics such as total power output, torque, and cadence, which would be of immediate interest to the cyclist during training for improving pedaling technique. Coaches and trainers may also observe a cyclist in action and provide feedback based on the displayed metrics, and in some embodiments may remotely adjust the crank angles and aural and haptic indicators through a separate device communicatively linked to the computing device 36 through a computer network. The system may be integrated with other measurement and monitoring systems to take other measurement quantities into account, such as heart rate, acceleration, and pedal pressure. It will be appreciated that other embodiments may divide the pedal crank cycle into a different quantity of divisions. For example, the selector 60 may consist of 28, 32, 36, or 40 divisions in the pedal crank cycle, so that each division represents 12.9, 11.3, 10, or 9 degrees of the crank rotation, respectively. It will be appreciated that these are merely examples and many other divisions could alternatively be employed.

The left pedal may be configured independently of the right pedal, so that different predetermined crank angles may be selected between the right and left pedals, which is especially applicable to pedaling devices used for training that allow each leg to cycle independently of the other, eliminating the contribution of the contralateral leg during any motion, and thereby enhancing the effectiveness of specific technique workouts during the upstroke phase. Cyclists may also choose to limit practice to either the right or left pedal for other phases of the pedal crank cycle, especially to develop the skill to ride without any dead spots at the top and bottom of the cycle. Consequently, a left switch 66A and a right switch 66B are provided on the GUI 58 to enable or disable the crank angle detector from detecting the left predetermined crank angle or right predetermined crank angle, respectively, and inhibiting the indicator from emitting an indication when said left or right predetermined crank angle is reached. Information on power, torque, cadence, and other metrics for each individual leg may be provided, in addition or alternatively to information for both legs combined, so that the cyclist's performance could be monitored more closely.

A menu bar 80 may be provided on the GUI 58, featuring a pause button 68, a graph button 70, a crank angle display button 72, a one-pedal display button 74, a two-pedal display button 76, and a record button 78. The user operates the pause button 68 to pause a recording operation or real-time display of information. The user operates the graph button 70 to view a graphical representation of power output, torque, cadence, and other metrics over time. The user operates the crank angle display button 72 to view the crank angle display, which provides a selector that divides the pedal crank cycle into multiple divisions, each of which is independently configurable by the user to be the left or right predetermined crank angles that determine the rotational angle range that is reached for the indication device to output an indicator. The one-pedal display button 74 provides the user the option to show information on only the left pedal or the right pedal on the display. The two-pedal display button 76 provides the user the option to show information on both the left pedal and the right pedal on the display. The user operates the record button 78 to start recording a training session, so that the recorded information may be reviewed and analyzed later.

Figure 5:
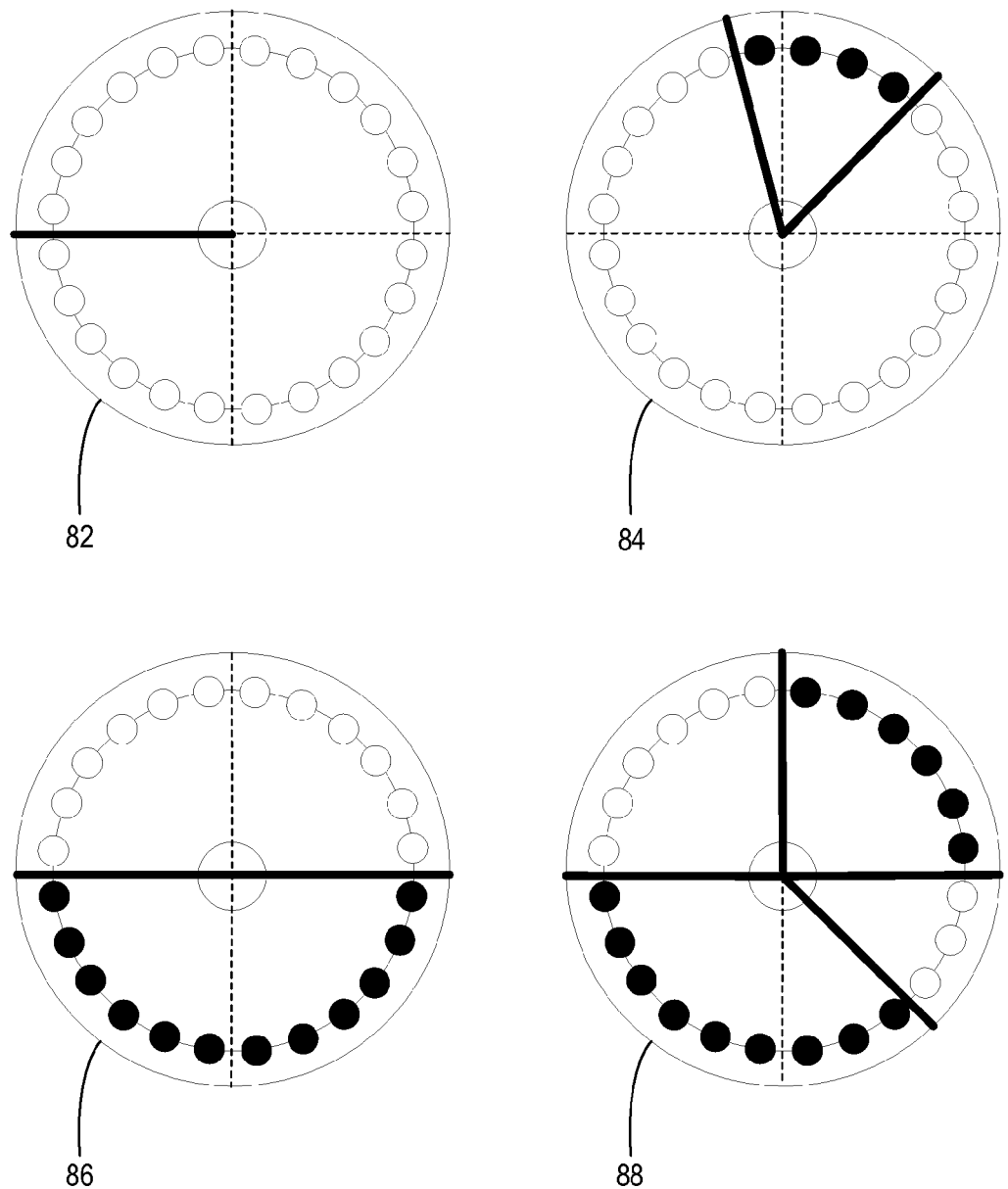
FIG. 5 is a schematic view of four of the possible user configurable settings on the GUI for the crank angle indication system.

Referring to FIG. 5, four of the many possible user configurable settings on the GUI for the crank angle indicating system are illustrated. With the configuration of FIG. 5, the GUI enables the user to choose to provide one, two, or four predetermined crank angles to set various rotational angle ranges, which, when reached, prompt the indication device 38 to output an indicator. In the first configuration 82, the GUI enables the user sets only one predetermined crank angle, which, when reached, causes the indication device to output an indicator for a brief, predetermined duration of time. In the second configuration 84, the GUI enables the user selects two predetermined crank angles, which set the rotational range that is reached for the indication device to output an indicator. In the third possible configuration 86, the GUI enables the user selects two predetermined crank angles that are substantially separated by 180 degrees, which set the rotational range that is reached for the indication device to output an indicator. In the fourth possible configuration 88, the GUI enables the user to select four predetermined angles, setting two rotational angle ranges that are reached for the indication device to output an indicator. It will be appreciated that, since each division in the pedal crank cycle is independently configurable, other crank angle and rotational range settings can be configured by the user.

Figure 6:
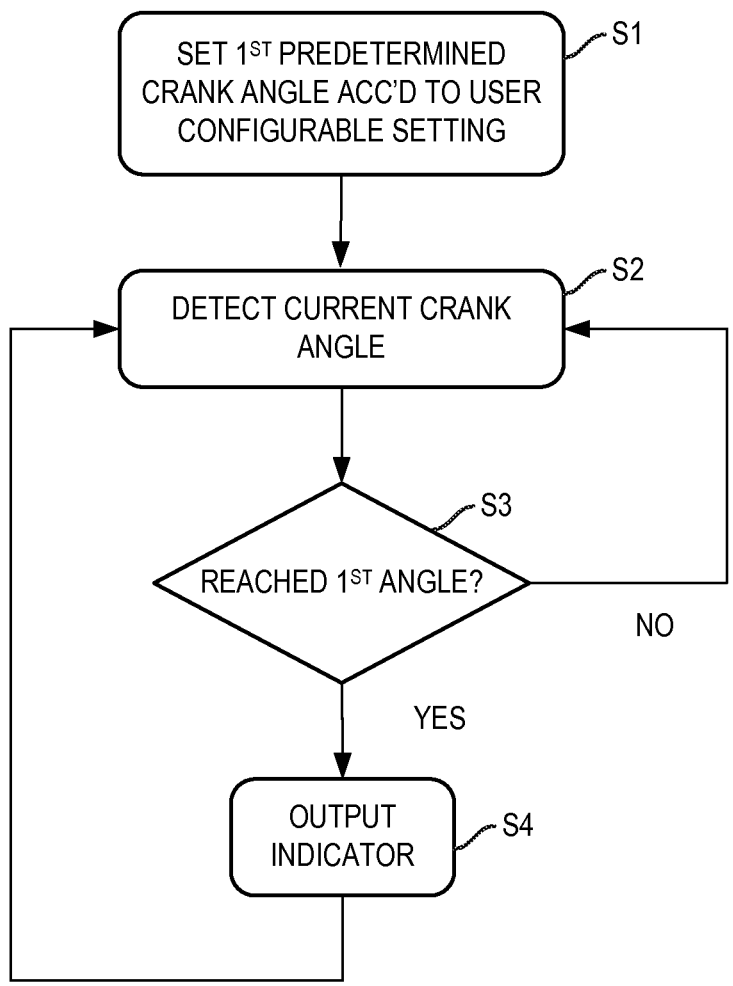
FIG. 6 is a flowchart illustrating exemplary program logic executed by the processor of a computing device that receives output from a crank angle detector and sends a signal to an indication device to output an indicator, when only one predetermined crank angle is provided, in accordance with an embodiment of the present disclosure.

Referring to FIG. 6, a flowchart illustrates a method implemented by program logic executed by the processor of computing device, which receives output from a crank angle detector 34 and sends a signal to an indication device 38 to output an indicator, when one predetermined crank angle is specified, in accordance with an embodiment of the present disclosure. At step S1, the user selects the first predetermined crank angle. At step S2, the crank angle detector detects a current crank angle and sends output to the computing device. At the step S3, if the computing device determines that crank angle has reached the first predetermined crank angle, the method proceeds to step S4, and when the result is NO, the method proceeds back to step S2. At step S4, the indication device outputs an indicator for a predetermined duration of time, then proceeds back to step S2.

Figure 7:
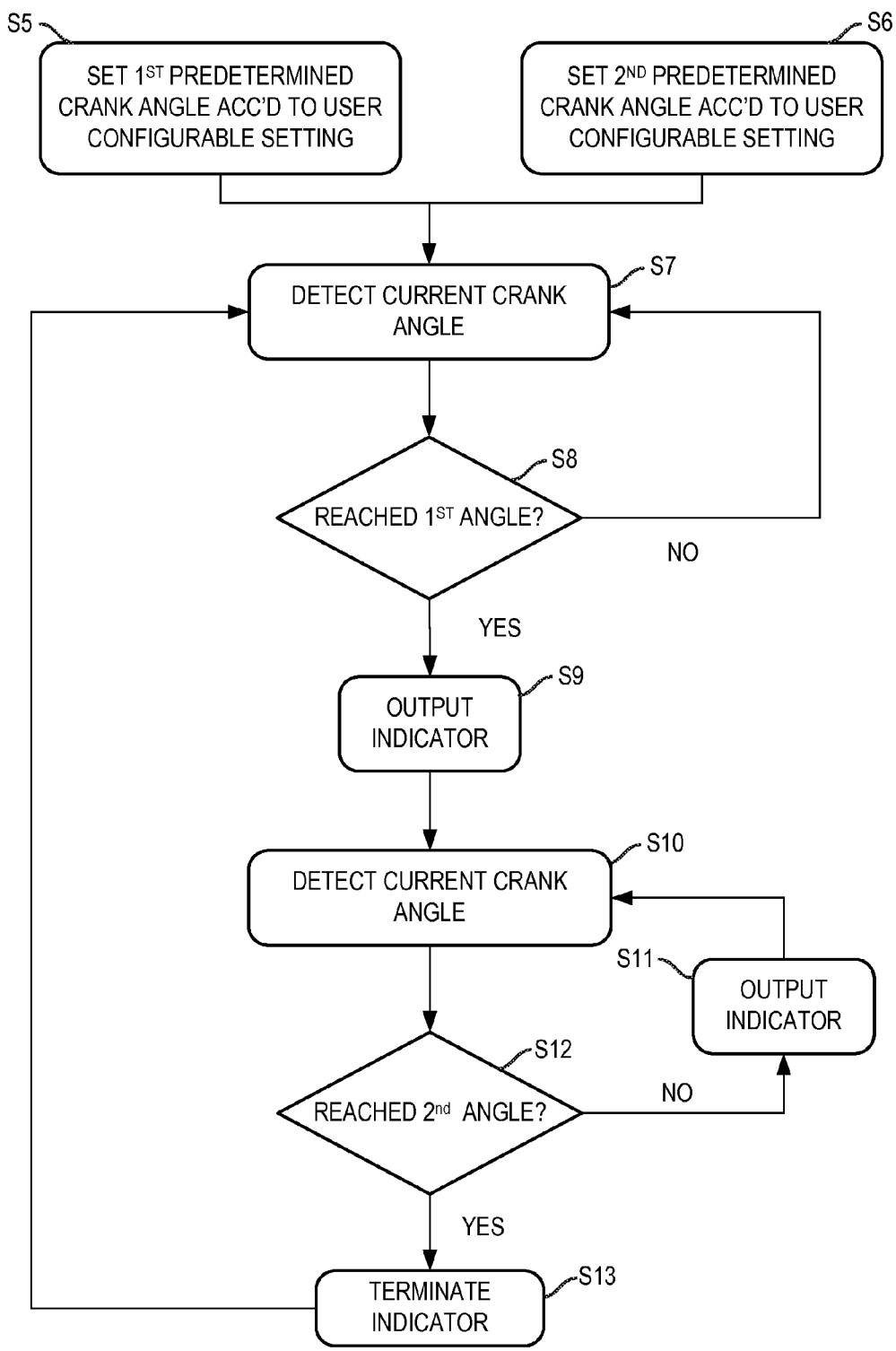
FIG. 7 is a flowchart illustrating exemplary program logic executed by the processor of a computing device that receives output from a crank angle detector and sends a signal to an indication device to output an indicator, when two predetermined crank angles are provided, in accordance with an embodiment of the present disclosure.

Referring to FIG. 7, a flowchart illustrates another method implemented by the program logic executed by the processor of a computing device 36, which receives output from a crank angle detector 34 and sends a signal to an indication device 38 to output an indicator, when two predetermined crank angles are provided, in accordance with an embodiment of the present disclosure. The user selects the first predetermined crank angle at step S5 and the second predetermined crank angle at step S6 on a GUI. At step S7, the crank angle detector detects a current crank angle and sends output to the computing device. At the step S8, if the computing device determines that crank angle has reached the first predetermined crank angle, the method proceeds to step S9 and outputs an indicator, and when the result is NO, the method proceeds back to step S7. After outputting an indicator at step S9, the crank angle detector again detects a current crank angle at step S10. At step S12, if the computing device determines that the crank angle has not reached the second predetermined crank angle, the method proceeds to step S11, outputting an aural or haptic indicator, then returning to step S10, and when the result is YES, the method terminates the indicator at step S13 and proceeds back to step S7.

Figure 8:
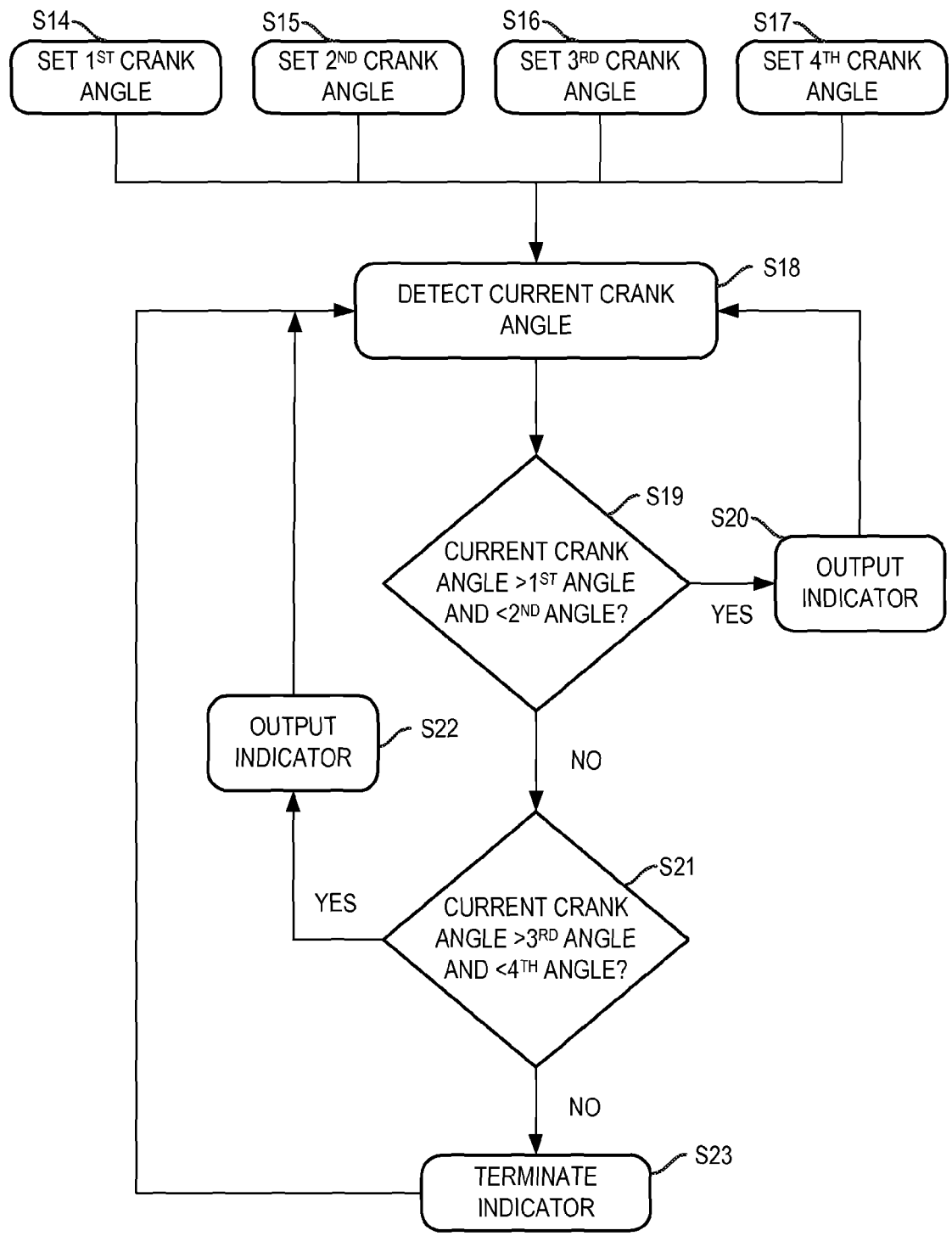
FIG. 8 is a flowchart illustrating exemplary program logic executed by the processor of a computing device that receives output from a crank angle detector and sends a signal to an indication device to output an indicator, when four predetermined crank angles are provided, in accordance with an embodiment of the present disclosure.

Referring to FIG. 8, a flowchart illustrates a method implemented by the program logic executed by the processor of computing device 36, which receives output from crank angle detector 34 and sends a signal to an indication device 38 to output an indicator, when four predetermined crank angles are provided, in accordance with an embodiment of the present disclosure. At steps S14 through S17, the user selects the first, second, third, and fourth predetermined crank angles on a GUI. At step S18, the crank angle detector detects a current crank angle and sends output to the computing device. At the step S19, if the computing device determines that current crank angle lies in the rotational range between the first and second predetermined crank angles, the method proceeds to step S20 and outputs an indicator, and when the result is NO, the method proceeds to step S21. At step S21, if the computing device determines that the current crank angle lies in the rotational range between the third and fourth predetermined crank angles, the method proceeds to step S22, outputs an indicator, and returns to step S18. When the result is NO, the method proceeds to step S23 and terminates the indicator before returning to step S18.

Figure 9:
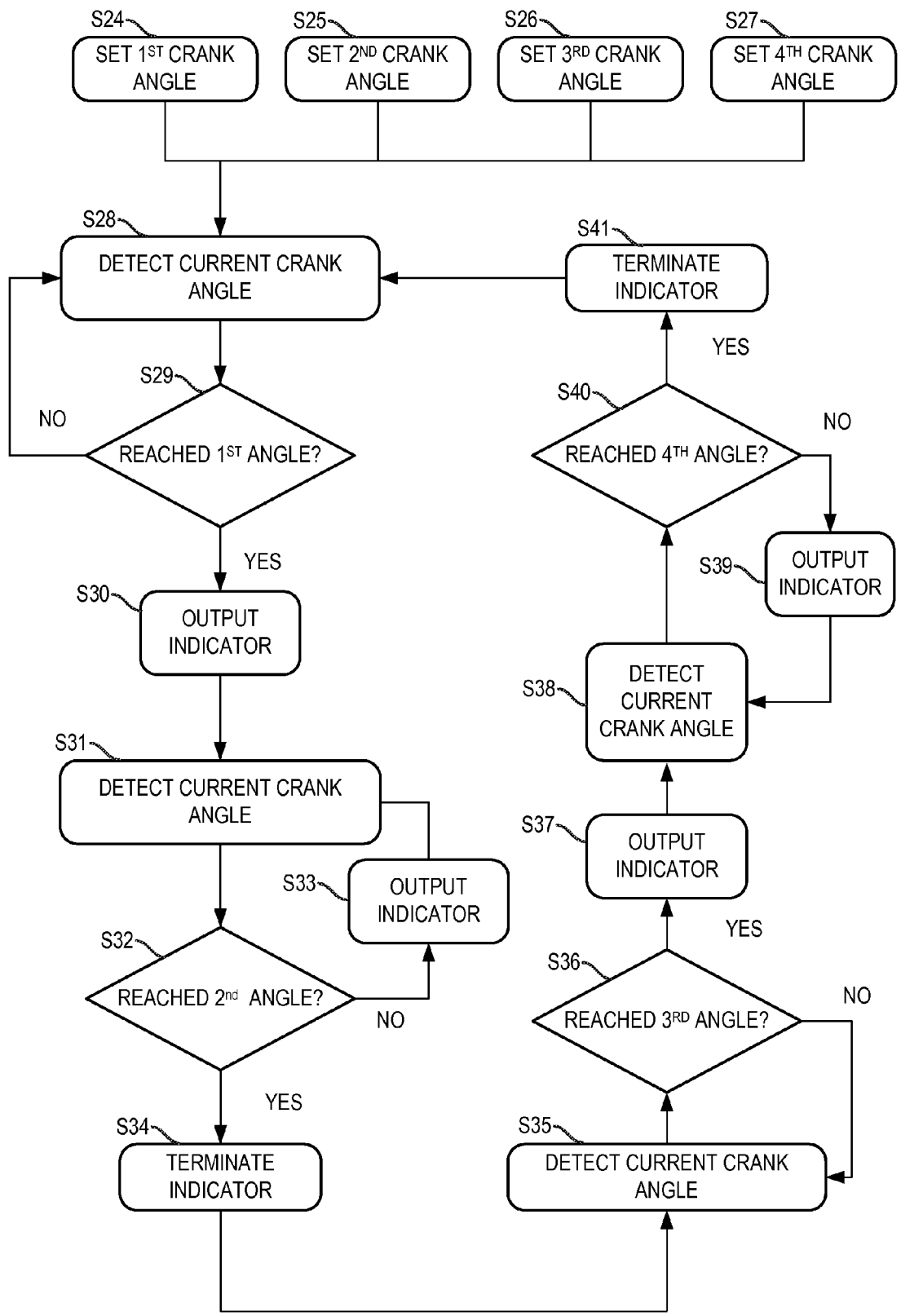
FIG. 9 is a flowchart illustrating another exemplary program logic executed by the processor of a computing device that receives output from a crank angle detector and sends a signal to an indication device to output an indicator, when four predetermined crank angles are provided, in accordance with an embodiment of the present disclosure.

Referring to FIG. 9, a flowchart illustrates an alternative method implemented by program logic executed by the processor of computing device 36, which receives output from a crank angle detector 34 and sends a signal to an indication device 38 to output an indicator, when four predetermined crank angles are provided, in accordance with an embodiment of the present disclosure. At steps S24 through S27, the user selects the first, second, third, and fourth predetermined crank angles on a GUI. At step S28, the crank angle detector detects a current crank angle and sends output to the computing device. At the step S29, if the computing device determines that the current crank angle has reached the first predetermined crank angle, the method proceeds to step S30, outputs an indicator, and proceeds to step S31, and when the result is NO, it proceeds back to step S28. At the step S31, the crank angle detector detects a current crank angle again and sends output to the computing device. If the computing device determines that the current crank angle has reached the second predetermined crank angle, the method proceeds to step S34, terminates the indicator, and proceeds to step S35. When the result is NO, the method proceeds to step S33, outputs an indicator, and returns to step S31.

At step S35, the crank angle detector detects a current crank angle and sends output to the computing device. At the step S36, if the computing device determines that the current crank angle has reached the third predetermined crank angle, the method proceeds to step S37, outputs an indicator, and proceeds to step S38, and when the result is NO, the method proceeds back to step S35. At the step S38, the crank angle detector detects a current crank angle again and sends output to the computing device. If the computing device determines that the current crank angle has reached the fourth predetermined crank angle, the method proceeds to step S41, terminates the indicator, and proceeds back to step S28. When the result is NO, the method proceeds to step S39, outputs an indicator, and returns to step S38.

The above embodiments provide a convenient and effective system and methods for enabling cyclists to receive cues to apply and/or release force on the pedal at the appropriate moment in the spin cycle of the crank gear.

The term "comprising" and its derivatives, as used herein, are intended to be open ended terms that specify the presence of the stated features, elements, components, groups, integers, and/or steps. This concept also applies to words of similar meaning, for example, the terms "have", "include" and their derivatives.

The term "pedaling device" and its derivatives, as used herein, are intended to be open ended terms that specify any vehicle or machine with a wheel that is propelled by the action of a cyclist's feet upon pedals, and encompasses outdoor bicycles, stationary bicycles, exercise cycles, indoor bicycles, and the like.

The terms of degree such as "approximately" as used herein mean a reasonable amount of deviation of the modified term such that the end result is not significantly changed (e.g., manufacturing tolerances).

While specific embodiments of the pedaling device and crank angle indicating system have been described in detail, the particular arrangements disclosed are meant to be illustrative only and not limiting. The features of the various embodiments described above, as well as modifications thereof, may be variously combined without departing from the scope of this disclosure.

The invention claimed is:

1. A crank angle indicating system, comprising:
    an input device of a computing device, the input device being configured to receive a user selection of one or a plurality of predetermined target crank angle ranges within a 360 degrees pedal crank cycle for each pedal of a pedaling device;
    a crank angle detector configured to detect a crank angle of a crankshaft of a pedaling device; and
    an indication device configured to output at least one of an aural and a haptic indicator upon the detected crank angle matching the user-selected one or plurality of predetermined target crank angle ranges for each pedal within the 360 degrees pedal crank cycle.

2. The crank angle indication system of claim 1, wherein the predetermined crank angle is set according to a user configurable setting.

3. The crank angle indication system of claim 1,
    wherein the predetermined crank angle is a first predetermined crank angle and the crank angle detector is further configured to detect a second predetermined crank angle; and
    wherein the indication device configured to output at least one of an aural and a haptic indicator upon the detected crank angle reaching the first predetermined crank angle and the second predetermined crank angle, respectively.

4. The crank angle indication system of claim 3, wherein the second predetermined crank angle is set according to a user configurable setting.

5. The crank angle indication system of claim 4, wherein the first predetermined crank angle and the second predetermined crank angle are different angles.

6. The crank angle indication system of claim 5, wherein the first predetermined crank angle and the second predetermined crank angle are left and right predetermined crank angles, respectively.

7. The crank angle indication system of claim 6, wherein the left and right predetermined crank angles are substantially separated by 180 degrees.

8. The crank angle indication system of claim 3, wherein the first indicator and the second indicator are aurally or haptically distinguishable.

9. The crank angle indication system of claim 1, wherein the at least one of an aural and a haptic indicator is emitted over a rotational angle range.

10. The crank angle indication system of claim 9, wherein an aural or haptic characteristic of at least one of an aural and a haptic indicator varies while being emitted over the rotational angle range.

11. The crank angle indication system of claim 1, further comprising;
    a processor executing program logic configured to receive the detector signal from the crank angle detector indicating a detected crank angle, and
    output an angle indication signal upon determining that the detected crank angle reaches a predetermined crank angle,
    wherein the indication device is configured to receive the angle indication signal and, in response, output at least one of an aural and a haptic indicator.

12. The crank angle indication system of claim 11, wherein the processor is a processor of an onboard computing device mountable to the pedaling device.

13. The crank angle indication system of claim 1, further comprising an input device configured to selectively activate and deactivate the indication device.

14. The crank angle indication system of claim 1, wherein at least one of the aural and a haptic indicator is an aural indicator, and the indication device is a speaker that emits the aural indicator.

15. The crank angle indication system of claim 14, wherein the speaker is located on an onboard computing device coupled to the pedaling device.

16. The crank angle indication system of claim 14, wherein the speaker is located in an earphone.

17. The crank angle indication system of claim 1, wherein at least one of an aural and a haptic indicator is a haptic indicator, and the indication device is a vibration device configured to emit vibration as the haptic indicator.

18. The crank angle indication system of claim 17, wherein the vibration device is coupled for vibrational transmission to at least one of a handlebar of the pedaling device, a seat of the pedaling device, a pedal of the pedaling device, and wristwatch of a rider of the pedaling device.

19. A crank angle indicating system, comprising:
an input device of a computing device, the input device being configured to receive a user selection of one or a plurality of predetermined target crank angle ranges within a 360 degrees pedal crank cycle for each pedal of a pedaling device;
a crank angle detector configured to detect a crank angle of a crankshaft of a pedaling device; and
an indication device configured to output an indicator to provide a cue for a rider to apply or release force on the pedals based on a current crank angle of the crankshaft of the pedaling device for each pedal within the 360 degrees crank cycle and the user-selected one or plurality of predetermined target crank angle ranges for each pedal.

* * * * *